United States Patent [19]
Howard

[11] Patent Number: 5,563,335
[45] Date of Patent: Oct. 8, 1996

[54] HIGH FLOW RATE SAMPLER FOR MEASURING EMISSIONS AT PROCESS COMPONENTS

[75] Inventor: Harry M. Howard, Moscow, Id.

[73] Assignee: Gas Research Institute, Chicago, Ill.

[21] Appl. No.: 396,403

[22] Filed: Feb. 28, 1995

[51] Int. Cl.[6] .................................................... G01M 3/18
[52] U.S. Cl. ........................................ 73/46; 73/863.33
[58] Field of Search ............................ 73/40, 40.5 R, 73/40.7, 46, 863.31, 863.41, 863.33, 863, 864.33, 864.34, 864.21, 23.21

[56] References Cited

U.S. PATENT DOCUMENTS

| | | | |
|---|---|---|---|
| 3,187,558 | 6/1965 | Koncen et al. | 73/24.03 |
| 3,786,675 | 1/1974 | Delatorre et al. | 73/40.7 X |

*Primary Examiner*—Michael J. Brock
*Attorney, Agent, or Firm*—Hill, Steadman & Simpson

[57] ABSTRACT

A new high flow rate sampling device and methods for measuring fugitive gas emissions are provided. The high flow rate sampler comprises an air mover connected to a flexible hose for drawing in air near a process component, such as a pump, compressor seal, flange, or pipe thread connection. A second sample hose draws air from the opposing side of the process component at a flow rate low enough not to affect capture of the leak by the first sample hose. Air measured from the first sample hose will contain fugitive emissions from the process component being measured, as well as from other process components. Air measured from the second sample hose will contain only fugitive emissions from surrounding process components and can then be subtracted from the measurement from the first sample hose to obtain the leak rate from the process component in question.

16 Claims, 6 Drawing Sheets

NO DILUTER - COMPLETE LEAK CAPTURE

NO DILUTER - INCOMPLETE LEAK CAPTURE

LEAKING COMPONENT
DILUTER OPERATION - COMPLETE LEAK CAPTURE

LEAKING COMPONENT
DILUTER OPERATION - INCOMPLETE LEAK CAPTURE

HIGH FLOW RATE SAMPLER FOR MEASURING EMISSIONS AT PROCESS COMPONENTS

FIELD OF THE INVENTION

This invention relates generally to the measurement of fugitive air pollution emissions from a wide range of processes utilized in the natural gas, petroleum, petrochemical, and chemical industries.

BACKGROUND

Fugitive emissions are air pollution emissions that are not released from stacks designed as release points. Instead, fugitive emissions escape from industrial processes by means such as evaporation from wastewater treatment areas or leaks at process components. Leaks may occur at process components such as pumps, compressor seals, flanges, valves, pipe thread connections, and open ended lines on valves that are shut off. Rising concerns over hazardous air pollutants and greenhouse gases have led to the need for improved quantification of fugitive emissions to the environment.

Fugitive emissions are very difficult to quantify without expensive and time consuming measurement programs. Consequently, the oil, gas, and chemical industries typically use techniques to estimate the emission rate. These techniques are easy to apply but have several large uncertainties inherent in there use, as described below.

All emission measurement methods rely on determining the concentration of the compound(s) being emitted from the source and an estimation of the amount of dilution that takes place between the source and the point of concentration measurement. For example, when using an enclosure technique, the leaking component is wrapped with a nonpermeable material and a clean purge gas (such as nitrogen) sweeps through the enclosure at a measured flow rate. The known flow rate of purge gas provides a known dilution rate of the compound(s) leaking from the component. In the case of methane ($CH_4$), the emission rate using an enclosure measurement can be calculated from the purge flow rate through the enclosure and the concentration of methane in the outlet stream as follows:

$$Q_{CH4} = F_{purge} \times C_{CH4} \times 10^{-6}$$

where:

$Q_{CH4}$=emission rate of methane from the enclosed component (ml/min), $F_{purge}$=the purge flow rate of the clean air or nitrogen (ml/min), and $C_{CH4}$=the measured concentration of methane in the exit flow (ppm).

The enclosure measurement technique is relatively accurate, but requires extensive time and effort to set up. Processes and components of concern must be carefully wrapped with the non-permeable material so that no unwanted gas or air enters the enclosure. The time and expense associated with this technique makes it prohibitive for routine monitoring of gas leaks.

Another technique to determine leak rate uses correlations which have been developed to relate the concentration measured near a leaking component to its actual leak rate. These relationships have been developed by correlating leak rates measured at components using the enclosure technique to the maximum concentrations measured at either 1 cm or 1 mm from the components using a portable volatile organic compound (VOC) analyzer. Correlations have been reported from work sponsored by the EPA (CMA, 1989) and the American Petroleum Institute (API) (Webb and Martino, 1992). These correlations essentially provide an empirical expression of the average dilution of the leaking material as it travels from the leak to the detector of the VOC. A plot of leak rate versus VOC screening value has been completed by others (CMA, 1989), and the scatter in measurements was demonstrated to be three orders of magnitude.

A theoretical ideal correlation between emissions and the resulting portable VOC analyzer screening concentration can be determined for a given VOC. This correlation depends on the volumetric sampling flow rate which is drawn into the instrument. If a methane leak is entirely captured by the instrument during screening, the concentration measured by the instrument will be:

$$C_{VOC} = \frac{Q_{LEAK}}{Q_{VOC}} \times 10$$

where:

$C_{VOC}$=concentration read by VOC (ppm), $Q_{LEAK}$=volumetric leak rate of methane from the component (ml/min), and $Q_{VOC}$=volumetric sampling flow rate of air drawn into the VOC (ml/min).

For instance, one commonly used instrument for screening components for fugitive emissions draws a nominal sample flow of 1000 ml/min. If a leak rate of 10 ml/min is entirely captured during screening, the resulting concentration will be 10,000 ppm, or 1%. Similarly, a leak rate of 1 ml/min would result in a VOC concentration of 1000 ppm, or 0.01%.

In practice, the actual ideal concentration is rarely achieved because the leak is not completely captured. The amount of the leak which is captured using this technique can vary significantly and is affected by the following: the sampling flow rate; the distance of the sampling probe from the leak; the ambient wind speed or air movement; and the characteristics of the leak such as its velocity upon leaving the component and the area over which the leak occurs. Larger sampling distances and increased ambient wind speeds reduce the influence of the sample flow on the air movement around the leak and give the plume from the leak more opportunity to diffuse away from the probe and avoid capture. For larger leaks, the plume may have enough momentum to overcome the flow field generated by the sampling flow. For leaks which escape from several points around a component, the area covered by the sampling probe flow rate may not be large enough to capture the plume.

For the foregoing reasons, there is a need for less time consuming, yet precise methodology for measuring fugitive air emissions. An instrument for performing this new methodology should allow for rapid, accurate and reliable quantification of emission concentrations from processes and components.

SUMMARY

The present invention is directed to an instrument for measuring air emissions which allows for rapid, accurate and reliable measurement of the emission rate of air pollutants from processes and components. An instrument for measuring fugitive air emissions having features of the present invention comprises an air mover capable of high flow rates for inducing a vacuum and an air flow measurement device which is connected to the air mover for measuring the rate of air flow. A first sample hose is connected to the air mover to draw air at a high flow rate to enhance capture of the air pollutants and can be positioned near a leaking component. A second sample hose, which can be connected directly to a gas analyzer, such as a portable VOC analyzer, draws air at a lower flow rate and is positioned on the opposite side of the leak being measured by said first sample hose. A means for connecting said instrument to a gas analyzer, such as a VOC analyzer, allowing for the concentration of the air pollutant to be determined if air is sampled from the first sample hose or for determination of background levels of contaminants if air is sampled from the second sample hose.

Alternatively, samples can be collected from the first and second sample hoses and analyzed at a later time. It is preferable that the flow rate in the first sample hose is adjustable, such as by attaching a gas regulator to the air mover, so that the vacuum created by the first sample hose can be adjusted for measuring leak rates under varying conditions. For example, breezy conditions at some sites may require a higher flow rate, ie. greater vacuum, to completely capture the leak, compared to a similar measurement indoors. Applying a high flow rate is an advantage of the present invention since the application of a high flow rate allows for a more complete capture of the gas emissions from leaking components.

A three-way valve can be used to allow for sample collection or analysis of air from the first sample hose or the second sample hose. Most preferably, a solenoid can be used for rapid and automatic switching between measurement of contaminants in the first and second sample hoses. Continuous application of the vacuum created by the first sample hose while measuring contaminants in the second sample hose allows for background measurements to be made, which can be high if surrounding leaking components are present. The near-simultaneous measurement of background levels of contaminants is an advantage of the present invention so that measured leak rates can more accurately be attributed to the appropriate components.

Data acquisition can also be used with the present invention to allow for computer control, calculation and recording of leak rate data. Connections from a computer control system to the flow meter, solenoid and gas analyzer would allow for almost operator-free operation of the high flow rate sampling instrument with minor modifications to existing computer hardware and software.

Another aspect of the present invention is a method for more accurately measuring fugitive air emissions. The method of the present invention comprises the steps of drawing air from one side of a leaking component into a sample hose at a high flow rate to dominate air movement near the leaking component and allowing for complete capture of the leak. Simultaneously, drawing air from the other side of the component into a second sample hose, at a low enough flow rate not to effect capture of the leak, to measure background concentration of the gas in air not influenced by the leak. Measuring the air flow rate using a flow meter to allow for calculation of the leak rate, and measuring the exit concentration of air pollutants in the air stream of the high flow sample hose and low flow sample hose using a gas analyzer, such as a portable volatile organic compound (VOC) analyzer.

BRIEF DESCRIPTION OF THE DRAWING

These and other features, aspects, and advantages of the present invention will become better understood with regard to the following description, appended claims, and accompanying drawings where:

Figure 1:
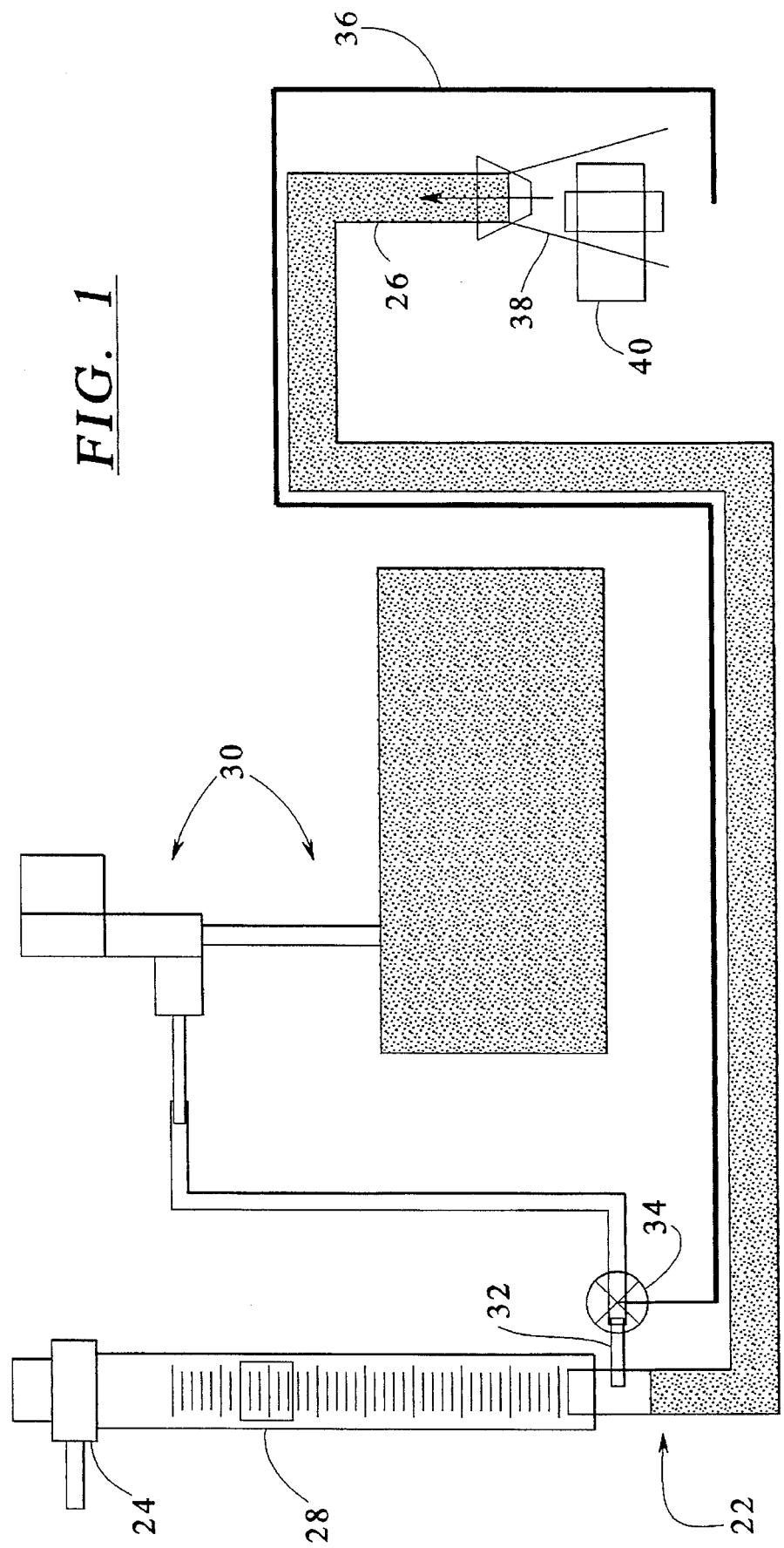
FIG. 1 is a schematic representation of one embodiment of a high flow rate sampler.

It should be understood that the drawings are not necessarily to scale and that the embodiments are sometimes illustrated by graphic symbols and diagrammatic representations. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION

Like reference numerals will be used to refer to like or similar parts from Figure to Figure in the following description of the drawings.

One embodiment of the new invention is shown in FIG. 1. An air mover 24 is used to draw the sampling flow through high flow rate sampler 22. The sample air is drawn through a first sample hose on line 26 and then through a rotameter 28, finally passing through the air mover 24. A sampling port 32 allows for high flow rate sampler 22 to be connected to volatile organic compound (VOC) analyzer 30.

The sample air flow may be varied by adjusting the pressure at the pneumatic air mover 24. The practical range of one current prototype is approximately 100 l/min to 500 l/min. However, other prototypes may be developed which may broaden this range. Two opposing factors influence the choice of sample flow rate for the system. Higher flow rates provide a better chance of complete leak capture especially if ambient winds are a factor or if the leak has significant momentum. However, higher flow rates also result in limits on the size of leak that can be quantified and increase the chance of interference from nearby leaks. For instance, at a sample flow rate of 100 l/min, a methane leak of 50 ml/min will result in a concentration increase of 500 ppm. A sample flow rate of 500 l/min at the same leak would result in a concentration increase of only 100 ppm. When working in an area where a high background concentration is present, a larger net concentration increase is easier to quantify. Optionally, a hood 38 is mounted on the end of first sample hose 26 to help capture the emission from a leaking component 40.

To conveniently determine the background concentrations of air pollutants near the component, a three way valve 34 is used to switch the instrument used to measure the concentration in the air sampling stream from the first sample hose 26 to a second sample hose on line 36, which runs along the first sample hose, and the open end of which is placed near the leaking component 40, but opposite first sample hose 26, during the leak measurement. The background concentration can then be determined under the same conditions of air movement that the sample concentration is measured. In particular, the leak being measured is not allowed to contribute to the background concentration as it would if the background concentration were measured without the high flow sampler in operation. This technique allows determination of background concentration without the need for a second instrument for analysis.

The known flow rate of the system provides the dilution rate from the source to sampling point. When complete leak capture is achieved, then the sampling system essentially performs an enclosure measurement where the leak is trapped by the flow regime of the high flow sampler instead of a physical enclosure. A volumetric emission rate can then be calculated in essentially the same manner as for an enclosure measurement:

$$Q_{AP} = F_{sampler} \times (C_{sample} - C_{back}) \times 10^{-6}$$

where:

$Q_{AP}$=the emission rate of air pollutants from the component tested (l/min), $F_{sampler}$=the sample flow rate of the high flow rate sampler (l/min), $C_{sample}$=the concentration of air pollutants in the sample flow (ppm), and $C_{back}$=the concentration of air pollutants in the background near the component (ppm).

Figure 2:
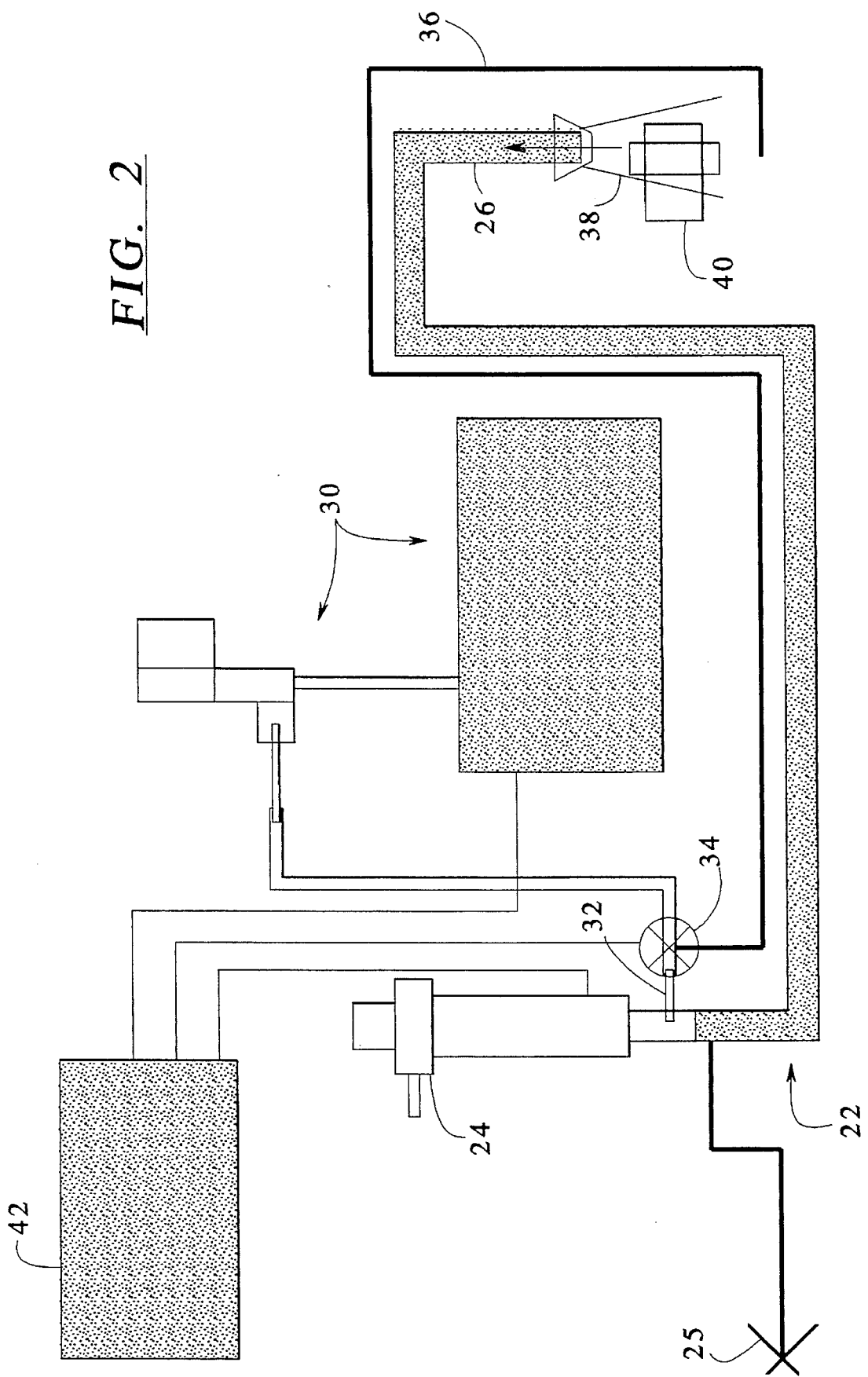
FIG. 2 is a schematic representation of a second embodiment of a high flow sampler used in conjunction with a data acquisition and control module.

FIG. 2 shows another embodiment of the present invention. A pneumatic air mover 24 is used to draw the sampling flow through the high flow rate sampler 22 to reduce the chance of sparking in an environment suspected of being contaminated with flammable gases. An additional feature, for intrinsic safety, is the use of a grounded, conductive first sample hose 26 during sampling to prevent any potential static charge buildup due to air flow through the hose. In the embodiment illustrated in FIG. 2, the conductive first sample hose 26 may include internal wire ribbing which can be grounded to prevent spark build-up. A fastener 25 can is used to ground high flow rate sampler 22 to any available grounded surface.

Also shown in FIG. 2 is the addition of a data acquisition and control module 42 to high flow sampler 22. Computer hardware and software can by used to control air flow, sampling time, and the recording of measurements. This would be particularly useful in hazardous environments or to conduct long term monitoring of fugitive emissions.

Example 1: Laboratory Validation Experiments

A series of experiments have been conducted to validate the results of the high flow rate sampler and to optimize the design. A simulated leak was used from which a known flow rate of methane was released.

The laboratory tests were conducted by releasing methane from a compressed gas cylinder through a two stage regulator and needle valve. The methane flow rate was measured using a one liter soap bubble meter (Alltech, Inc.) Methane flow rates were measured before and after each sampling period and had a nominal range of 0.5 l/min to 11 l/min. (All volumetric flow rates have been converted to conditions at 70° F., 1 atm.) Two different diameters of tubing were used for the release configuration, one with ¼" O.D. (approximately ³⁄₁₆" I.D.) and one with ⅛" O.D. (approximately ³⁄₃₂" I.D.). These different release diameters were used to investigate the effects of the leak exit velocity on the ability of the high flow sampler to completely capture the leak. Although the momentum of the leaking flow is probably a more accurate parameter, the exit velocity has been used to give a simple first approximation.

A series of sampling positions and distances were tested to see if complete capture of the leak could be achieved. As the reference case for complete capture, the release tube was placed inside the high flow sampler hose. This provided a calibration of the entire system, allowing the combined measurements of the sampler flow rate by rotameter and of the concentration of methane in the sample stream by OVA to be evaluated against the measured leak release rate. Three positions were then tested to determine how sensitive the system was to distance from the leak and the angle between the leak flow and sample flow. These positions were: (a) downstream of the leak (leak and sample flows parallel); (b) a 45° angle between leak flow and sample flow; and (c) a 90° angle between leak flow and sample flow. These positions were tested in still air and at wind velocities generated in the laboratory of approximately 2.5 and 4.5 m/s.

Any decreases in the concentration of methane measured in the sample flow as compared to the reference case would have indicated that complete capture of the leak was not obtained. However, complete leak capture was indeed possible for all conditions tested, as indicated by the ability to maintain the concentration measured in the reference case. The results of these tests using the ¼" O.D. release tube are shown in Table 1. As expected, the higher leak rates required that the sample inlet be held closer to the leak opening. The introduction of ambient air movement and the use of a lower sample flow rate also required the sample inlet to be held closer to the leak opening to maintain complete leak capture. Nevertheless, the concentrations and leak rates calculated from the high flow data shown in Table 1 were maintained for each test position. The agreement to the bubblemeter measurements made of the leak was within 5% for most measurements with a maximum deviation of 12%.

The most difficult leak capture test was position (c) with the sample flow at a 90° angle to the leak flow. In this position, the sampler inlet could not physically impede the momentum of the leak flow and the capture had to be caused by the induced flow from the sampler alone. For the flow rate of 517 l/min in still air, the sample inlet could be positioned as far away as 5 cm in this position for leak flows up to 7.05 l/min from the ¼" O.D. tube (exit velocity approximately 6.6 m/s). When the leak rate was increased to 10.95 l/min (exit velocity approximately 10.3 m/s), the sample inlet had to be within 3–4 cm of the leak. A flow rate of 11 l/min through the ⅛" O.D. release port (exit velocity approximately 41 m/s) required that the sampler inlet be within 1 cm to obtain complete leak capture with a sampling flow rate of 517 l/min.

Similarly, the lower sample flow rate of 262 l/min required closer sampling distances to obtain complete leak capture. Nevertheless, this sample flow rate could completely capture of leak rates up to 8 l/min (the highest tested) from the ¼" O.D. release port (exit velocity approximately 7.6 m/s) at distances up to 3 cm when the leak and sample flows were perpendicular. However, this sampling distance had to be reduced to 0.5 cm when the same sample flow was released from the ⅛" O.D. release port (exit velocity approximately 29.8 m/s).

Ambient air movement greatly reduced the maximum allowable distance of the sample inlet from the leak for complete leak capture. However, complete leak capture could be obtained even at wind speeds of 4.5 m/s by keeping the sample inlet within 0.25 cm of the leak for a sample flow rate of 517 l/min and within 0.1 cm for a sample flow rate of 262 l/min.

The ability of the high flow sampler to effect leak capture deteriorated as much as a factor of two outside the maximum sampling distances indicated. This effect is likely due to the relatively high momentum and orientation of the artificial leaks created in the laboratory and probably represents a worst case scenario. Most leaks in actual practice are more diffuse and consequently have less momentum.

The concentration range measured in the sample flow did not vary significantly between the known complete capture case (when the leak tube was inside the sample inlet and the other test positions. These concentration changes are probably due to minor flow and mixing variations within the high flow sampler. It should also be noted that the best agreement of the leak flow rate measured by bubblemeter and by the high flow sampler was when the concentration in the sample flow was in the range of 10,000 ppm and under. Since the concentrations in the sample flow were the same for the known complete capture case and the test positions (i.e., complete capture was maintained) the inaccuracies are due to the increased difficulty of calibrating the TVA-1000 for ranges above 10,000 ppm.

At larger leak rates, higher leak exit velocities, or higher ambient wind speeds, the high flow rate sampler can use a shield or partial enclosure to ensure successful leak capture. We are currently experimenting with a 6" diameter rubber hood split on each side. This hood can be placed over a variety of leak configurations to reduce the ambient wind speed effects and to help trap the emissions from the leak. Further testing to optimize this hood is underway.

Example 2: Field Demonstration of the High Flow Sampler

As indicated previously, the high flow sampler allows an accurate emission rate to be made in less than one tenth the time required to perform an enclosure measurement. Consequently, the high flow sampler make it possible to accurately quantify leak emission rates from leaking components instead of estimating the emission rates from screening correlations. The implications are two fold. First, emissions can now be quantified far more accurately than was ever possible before. Previously it has been uneconomical to perform enclosure measurements at all leaking components or even at all the components which resulted in "pegged source" (off scale) screening values. Additionally, with the leak rate database that can be generated for a specific facility, the largest leaks can be targeted for priority repair. Generally, the majority of emissions result from a relative small fraction of the leaking components. Repair of the large leaks allows large (and quantifiable) reductions in emissions in an economic manner.

Figure 3:
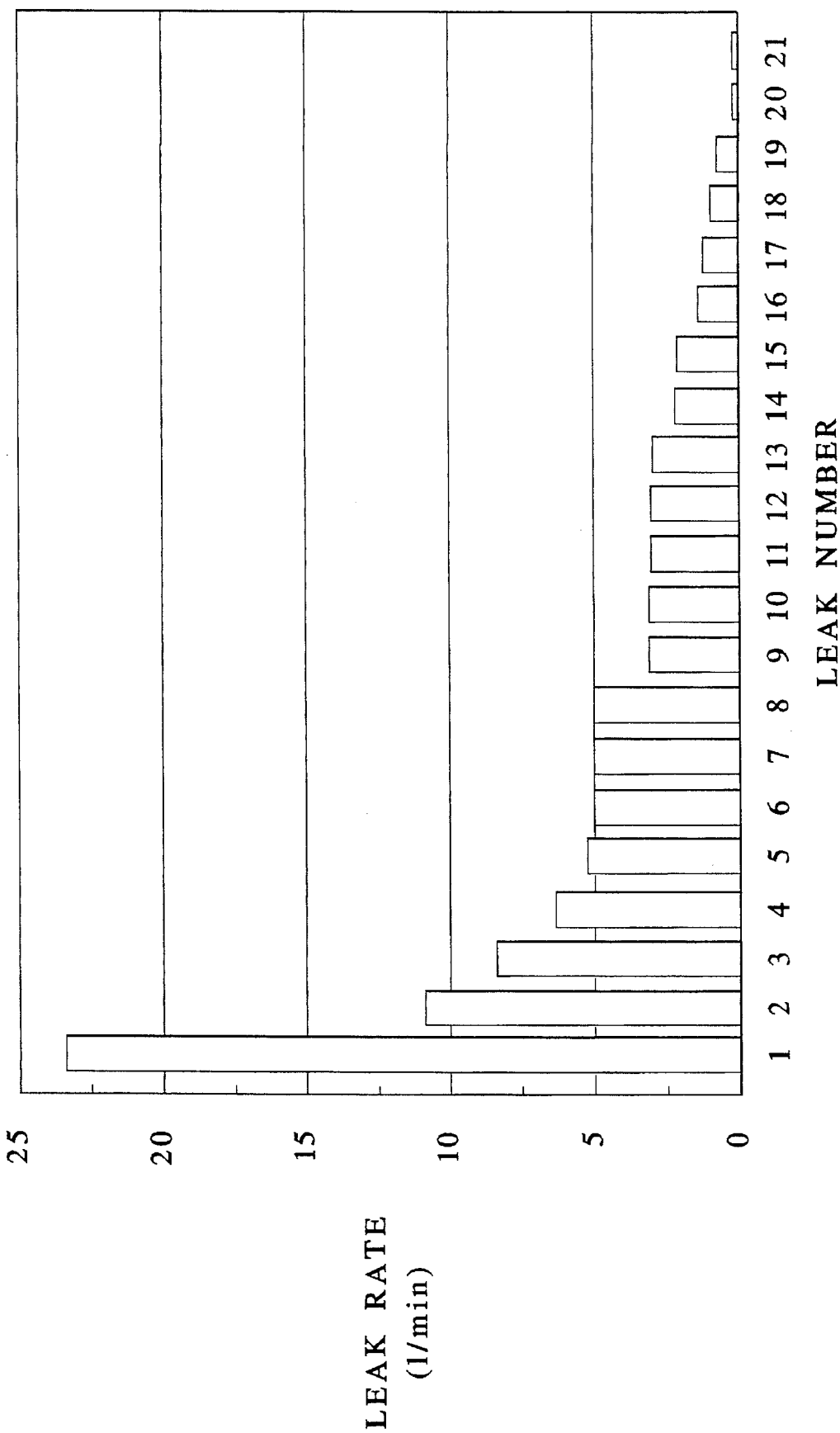
FIG. 3 is a bar graph illustrating the distribution of leak rates from "pegged source" compressor flanges.

The high flow sampler has been used to perform emission measurements at natural gas transmission pipeline compressor stations. At one site, 21 out of 64 flanges (33%) covering gas valves on compressors blew out the flame on the organic vapor analyzer (OVA-108) during screening (no diluter was used). This is equivalent to a concentration of approximately 90,000 ppm. The high flow rate sampler (with the sample flow rate set at nominally 450 l/min) was then used in conjunction with a Foxboro TVA-1000 to measure the leak rates from those 21 flanges. The leak rates (70° F., 1 atm) ranged from 0.12 l/min to 23.4 l/min, with an average of 4.49±5.01 l/min. The total leak rate from the leaking compressor flanges was 94.2 l/min. These measurements are presented in Table 1 and a distribution of the leak rates is shown in FIG. 3.

TABLE 1

Measurements of Methane Leak Rates from Compressor Valve Flanges at a Natural Gas Transmission Compressor Station.

| Leak No. | High Flow Sample Rate (l/min) | Net Sample Stream Concentration (ppm) | Methane Leak Rate (l/min) |
| --- | --- | --- | --- |
| 1 | 468 | 50050 | 23.42 |
| 2 | 432 | 25500 | 11.02 |
| 3 | 461 | 18600 | 8.57 |
| 4 | 446 | 14700 | 6.56 |
| 5 | 461 | 11300 | 5.21 |
| 6 | 468 | 10600 | 4.96 |
| 7 | 432 | 11440 | 4.94 |
| 8 | 468 | 10524 | 4.93 |
| 9 | 468 | 6800 | 3.18 |
| 10 | 468 | 6800 | 3.18 |
| 11 | 454 | 6900 | 3.13 |
| 12 | 446 | 6900 | 3.08 |
| 13 | 468 | 6500 | 3.04 |
| 14 | 461 | 4800 | 2.21 |
| 15 | 468 | 4500 | 2.11 |
| 16 | 439 | 3200 | 1.41 |
| 17 | 461 | 2658 | 1.22 |
| 18 | 446 | 2300 | 1.03 |
| 19 | 439 | 1700 | 0.75 |
| 20 | 432 | 400 | 0.17 |
| 21 | 446 | 280 | 0.12 |

Ave. leak rate = 4.49 l/min, Standard dev. = 5.01 l/min, Total leak rate = 24.9%, Largest 3 leaks = 45.6%

By fixing the largest leak only, emissions from this area of the station could be reduced by almost 25%. The four largest leaks represent over one half of the emissions from the flanges. Clearly, a data base of actual leak rates is a powerful tool in the preparation of an economical strategy for emissions reduction. Previous to this work, screening techniques would have identified these 21 flanges as pegged source emitters. However, there would have been no way of knowing which leaks should receive priority repair or what the actual emissions reduction would be if repairs were made, unless time consuming and expensive enclosure techniques were employed.

The use of screening concentrations measured at leaking process components to estimate emission rates may produce very uncertain results. Many factors affect the amount of dilution of the leaking material as it travels from the leak to the sample probe of the measuring instrument. These factors include the instrument sample flow rate, the sample probe distance from the leak, use of a diluter probe, ambient air movement, and individual leak characteristics such as velocity and leak rate.

Because sample flow rate affects the screening concentrations measured at a leak, the correlation of emissions versus concentration developed using a given organic vapor analyzer (OVA) will not be appropriate for use with a different OVA if the sample flow rates are significantly different. Screening concentrations must also be measured using the same sample probe distance as that used in the development of an emissions correlation. Use of a diluter probe in general will lead to extremely misleading results.

A high flow rate sampler has been developed to overcome the uncertainties of screening methods while reducing costs associated with time consuming enclosure studies. This sampler has been designed to be an accessory to currently available organic vapor analyzers. This new sampling system uses a high flow rate of air to effect complete capture of the emissions from a leaking component. The emission rate from the component is then calculated using the known sample flow rate and the concentration in the sample flow stream, with the local background subtracted.

The high flow sampler has been tested under laboratory conditions to determine its ability to measure known leak rates of various sizes and under different ambient conditions. It can easily measure leaks of at least 11 l/min with an accuracy of better than 10% of the true leak rate. However, it requires less than 10% of the time required to perform an enclosure measurement for a given component.

Example 3: Comparison of present invention to existing techniques

Figure 4:
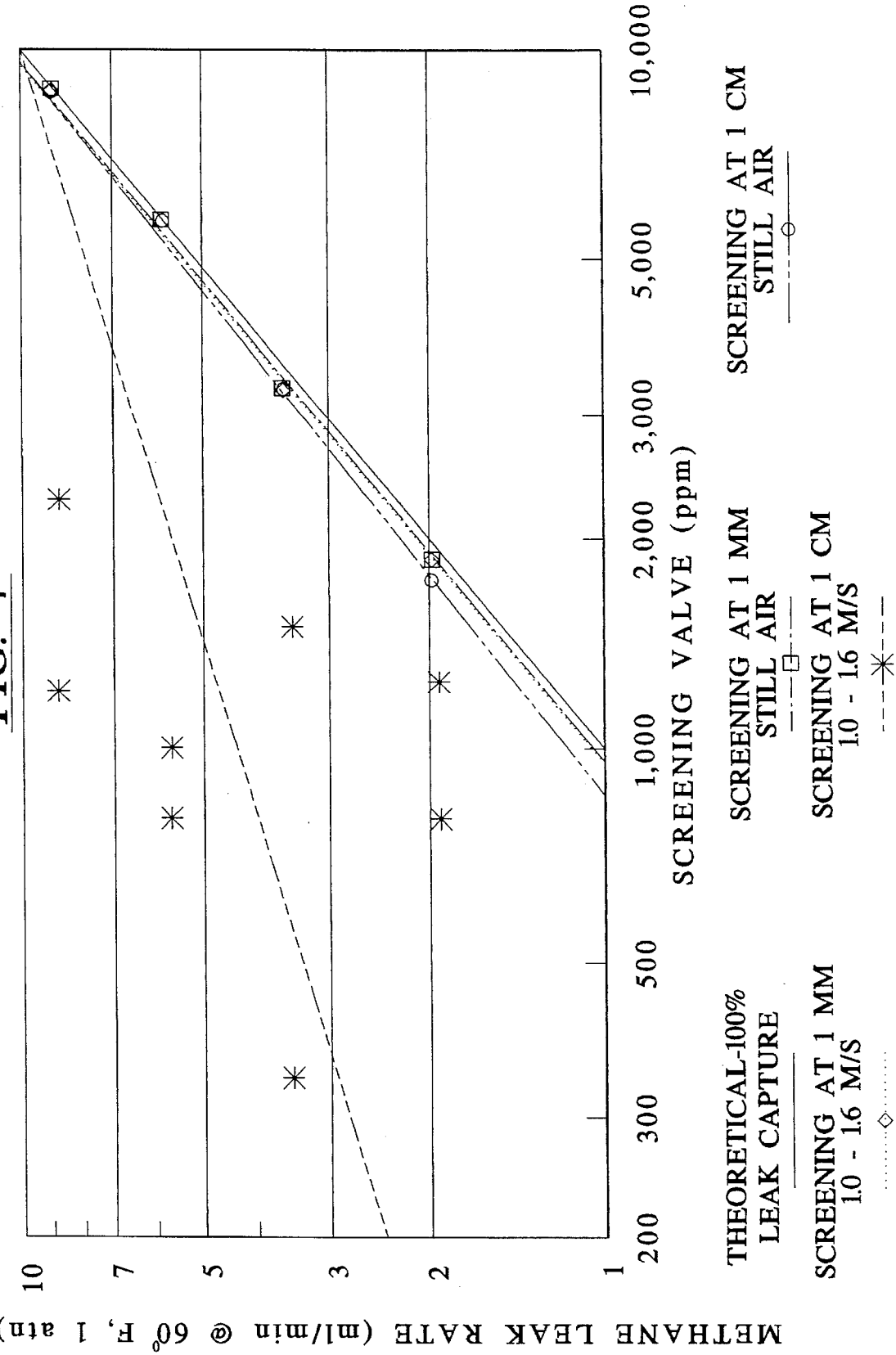
FIG. 4 is a graph illustrating the relationship between the methane emission rate and the screening value as taken from laboratory measurements.

To quantify the variation in the screening concentration as a function of wind speed, we made measurements under laboratory controlled conditions. Methane was released from a $1/16"\times 0.004"$ flow restrictor secured to a $1\frac{1}{4}"$ diameter pipe to simulate a methane leak at a component. The release rate was measured using a soap bubble meter. The release rate of methane was varied between 1.97 ml/min and 8.89 ml/min. Screening measurements were made at 1 mm and 1 cm sampling distances in still air (air movement <0.1 m/s) and at wind speeds generated by a 20" fan ranging from 1.0 to 1.6 m/s as measured by a vane anemometer. The results are shown in FIG. 4. At a sampling distance of 1 mm, the screening values are close to the theoretical 100% capture curve in both still air and when the fan was on. At a sampling distance of 1 cm, the screening values are still relatively close to the theoretical curve. However, when the fan was on, the screening values ranged from a factor of 2 to a factor of 10 lower than the theoretical curve. Since the inlet velocity of the sampling flow is approximately 2.1 m/s (as calculated from the inlet flow of 1000 ml/min and the inside diameter of the probe of $1/8"$), it is not surprising that ambient wind speeds in the same range would dominate the flow around the leak at a distance of 1 cm. Since these relatively light wind conditions had a drastic effect on the screening values under ideal conditions, it is likely that changes in wind speed alone may account for a large amount of the scatter seen in many correlations of emissions and screening values. Variation of measurements in the field indicates that higher wind speeds also affect the leak capture at a probe distance of 1 mm.

Figure 5A:
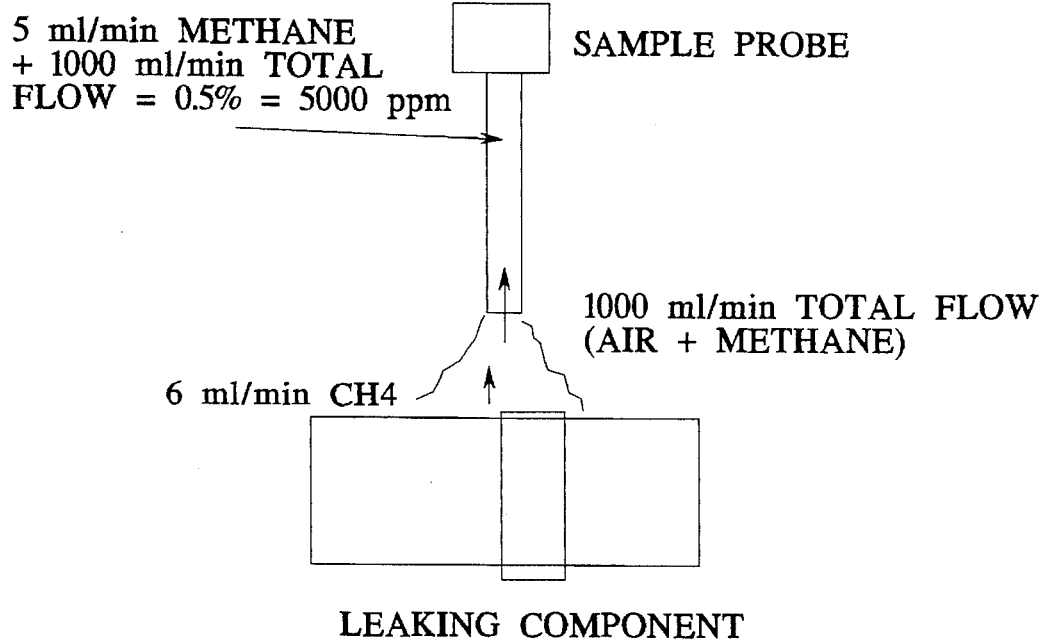
FIG. 5 is an illustration of the effect of leak rate and plume capture on OVA screening concentrations without diluter attachment.
Figure 5B:
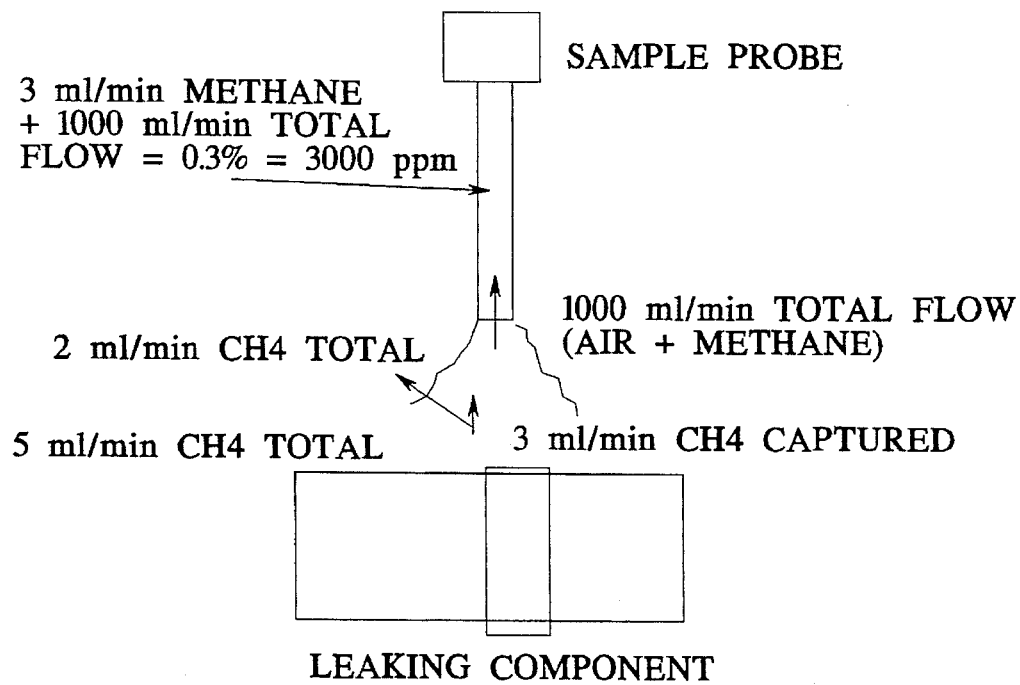

Many correlations have been developed based on the Foxboro OVA-108 which has a sample intake flow of approximately 1000 ml/min. It is important to note that these correlations will not be appropriate for use with screening data made with instruments that have a different sampling flow rate. We emphasize that this is not due to calibration differences, since a consistent calibration procedure will account for the difference in response factors between instruments. However, different sampling flow rates will affect the concentration resulting from a given leak rate for two reasons. First, instruments with higher sampling flow rates will tend to capture more of the plume from the leak than instruments with a lower sampling flow rate. Second, as discussed previously, the concentration that the instrument detector measures is a result of the amount of the methane plume from the leak entering the sample probe and the total volumetric flow rate into sample intake. Examples are shown in FIGS. 5(a) and 5(b). Although the Foxboro OVA-108 is a commonly used instrument for screening measurements, gas distribution companies often use different instruments for their screening work. One common instrument is the Southern Cross Model 400 Flame Pack. This instrument has a sample intake flow rate of 230 ml/min, less than 25% of the sample flow rate of the OVA-108. If a leak of 1 ml/min were completely captured using an OVA-108, the resulting screening concentration would be 1000 ppm. If the same leak were completely captured using Southern Cross Model 400, the screening concentration would be 4350 ppm due to the lower total flow rate into the instrument. This increased concentration may be offset somewhat by the reduced plume capture in actual screening applications, but there is no data available at this time to demonstrate how emissions estimated using instruments with different flow rates compare to each other. If an instrument with a lower flow rate results in consistently higher concentrations, the use of the existing correlations to estimate emissions will overestimate the actual emissions.

Figure 6A:
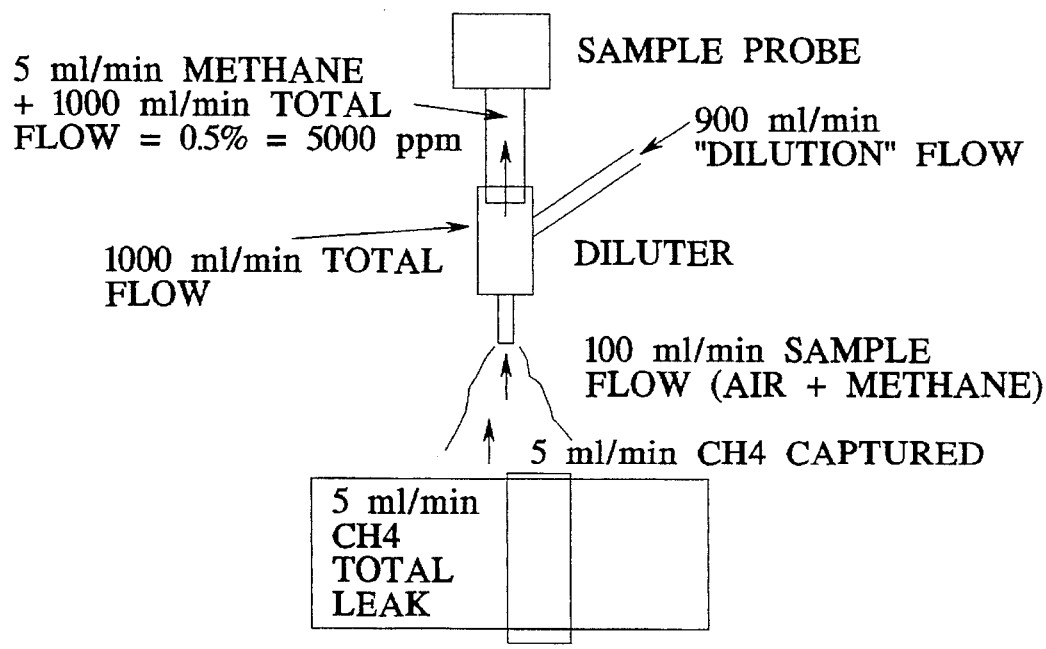
FIG. 6 is an illustration of the effect of leak rate and plume capture on OVA screening concentrations with diluter attachment.
Figure 6B:
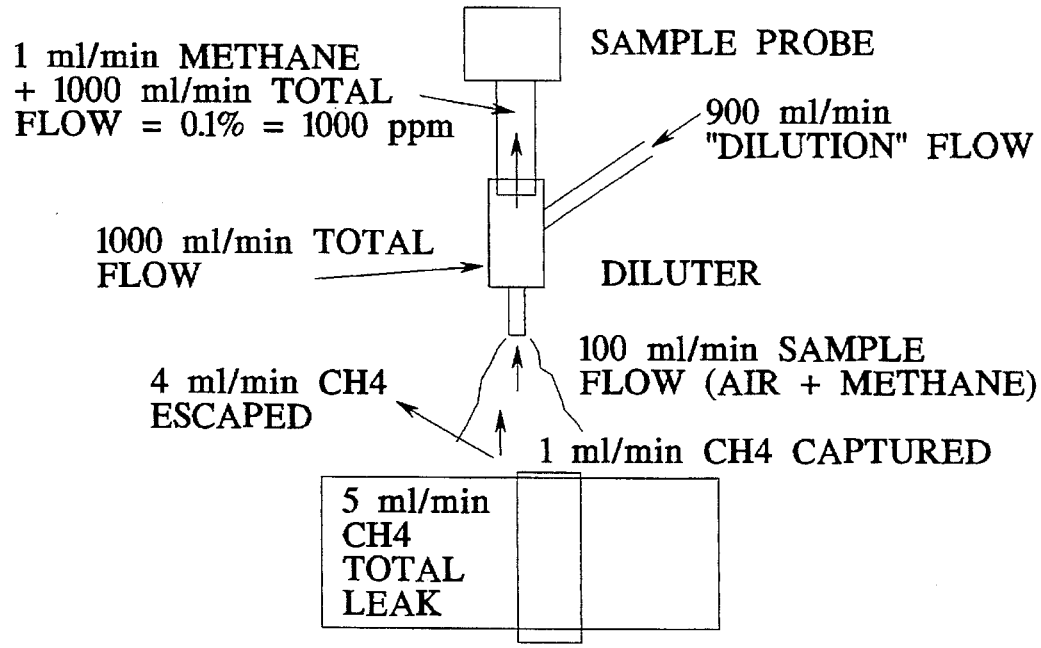

Diluters in the 10:1 range are often used with the Foxboro OVA. These diluters are actually flow restrictors which reduce the sample flow at the inlet to approximately 100 ml/min. Clean make-up flow (either filtered or from an external source) is supplied at approximately 900 ml/min. This lower sample inlet flow reduces the ability of the sample inlet to capture the leak. Measurements made with and without a diluter at the same leak will generally not be consistent. If complete capture of the leak occurred with the diluter, the resulting concentration measured with the OVA would in fact be the same as the concentration measured if complete capture occurred without the diluter. This is illustrated in FIGS. 6(a) and (b). This occurs because the total flow into the instrument in either case is approximately 1000 ml/min. With the diluter tip attached, it would be erroneously assumed that the concentration measured should be multiplied by a factor of 10. In practice, the restricted sample inlet flow may cause the amount of leak capture to vary either above or below the factor of 10 reduction implied by the use of the diluter. Because the reduced sampling flow at the component is more easily dominated by ambient air movement, it is more difficult to obtain consistent screening measurements when a diluter is used.

Although only two embodiments of the present invention have been illustrated and described, it will at once be apparent to those skilled in the art that variations may be made within the spirit and scope of the invention. Accordingly, it is intended that the scope of the invention be limited solely by the scope of the hereafter appended claims and not by any specific wording in the foregoing description.

I claim:

1. An apparatus for measuring gas leaking from a process component, the apparatus comprising:

a first sample hose having a first end and a second end, the first end of the first sample hose being disposed adjacent to the process component, the second end of the first sample hose being connected to an air mover, the air mover for drawing air and leaking gas through the first sample hose by way of a vacuum, a second sample hose having a first end and second end, the first end of the second sample hose being disposed adjacent to the process component but opposite the process component from the first end of the first sample hose, the second sample hose providing a conduit for background air, a gas analyzer connected to the second end of the first sample hose and the second end of the second sample hose, the gas analyzer for measuring the leaking gas being drawn through the first sample hose and the background air passing through the second sample hose.

2. The apparatus of claim 1,
further comprising a means for providing a flow rate in the second sample hose which is lower than that in the first sample hose.

3. The apparatus of claim 2,
further comprising an air flow measurement device connected in line with the air mover.

4. The apparatus of claim 2,
wherein the air mover is pneumatic.

5. The apparatus of claim 2,
wherein the first and second sample hoses contain an internal wire ribbing which can be grounded to prevent spark build-up.

6. The apparatus of claim 2,
wherein the air mover is adjustable to effect a flow rate through the first sample hose in the range 50 to 2,000 liters of air per minute.

7. The apparatus of claim 2,
wherein the means for providing a flow rate in the second sample hose allows for a flow rate through the second sample hose of less than 100 liters of air per minute.

8. The apparatus of claim 2,
further comprising a three way valve which allows for alternating measurements of air flowing through the first sample hose and the second sample hose.

9. The apparatus of claim 8,
further comprising a data acquisition system to allow for computer control, calculation and recording of leak rate data base on the leaking gas measured in the flow through the first sample hose and the background air measured in the flow through the second sample hose.

10. A process for measuring fugitive gas emissions from components, the process comprising the steps of:
   (a) creating a vacuum for drawing air into a first sample hose and a second sample hose;
   (b) drawing air, from near a component to be tested for fugitive emissions, into the first sample hose at a flow rate greater than 50 liters of air per minute; and
   (c) drawing air, from near the component, into the second sample hose at a flow rate which is low enough not to affect capture of the emissions by the first sample hose.

11. The process of claim 10,
further comprising the following step: (d) measuring the concentration of fugitive gas emissions in the air drawn into the first and second sample hoses.

12. The process of claim 11,
wherein the step (b) of drawing air into the first sample hose is at a flow rate greater than 150 liters of air per minute.

13. The process of claim 11,
wherein the step of measuring the concentration of fugitive gas emissions is performed using a volatile organic compound analyzer.

14. The process of claim 13,
further comprising the following step: (e) controlling one or more of the steps by a computer, wherein the computer has software for recording and calculating the concentration of the emissions.

15. An apparatus for measuring gas leaking from a process component, the apparatus comprising:
   a first sample line including a first end and a second end, the first end of the first sample line being disposed adjacent to the process component, the second end of the first sample line being connected to an air mover,
   the air mover for drawing air and leaking gas through the first sample line by way of a pressure drop,
   a second sample line having a first end and second end, the first end of the second sample line being disposed adjacent to the process component but opposite the process component from the first end of the first sample line, the second sample line providing a conduit for background air,
   an analyzer connected to the second end of the first sample line and the second end of the second sample line, the analyzer for measuring the leaking gas being drawn through the first sample line and the background air passing through the second sample line.

16. A process for measuring fugitive gas emissions from components, the process comprising the steps of:
   (a) creating a pressure drop for drawing air into a first sample line and a second sample line;
   (b) drawing air, from near a component to be tested for fugitive emissions, into the first sample line at a flow rate greater than 50 liters of air per minute; and
   (c) drawing air, from near the component, into the second sample line at a flow rate which is low enough not to affect capture of the emissions by the first sample line.

\* \* \* \* \*